(12) United States Patent
Liu et al.

(10) Patent No.: US 12,402,859 B2
(45) Date of Patent: Sep. 2, 2025

(54) CLASSIFICATION DISPLAY METHOD OF ULTRASOUND DATA AND ULTRASOUND IMAGING SYSTEM

(71) Applicant: SHENZHEN MINDRAY BIO-MEDICAL ELECTRONICS CO., LTD., Guangdong (CN)

(72) Inventors: Shuo Liu, Shenzhen (CN); Lang Lang, Shenzhen (CN); Jianguang Zhu, Shenzhen (CN); Zhijie Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 130 days.

(21) Appl. No.: 17/973,067

(22) Filed: Oct. 25, 2022

(65) Prior Publication Data
US 2023/0135046 A1    May 4, 2023

(30) Foreign Application Priority Data

Oct. 29, 2021  (CN) .......................... 202111272822.1

(51) Int. Cl.
*A61B 8/00* (2006.01)
*G06T 7/00* (2017.01)
*G06V 10/74* (2022.01)
*G06V 10/764* (2022.01)
*G06V 20/40* (2022.01)

(52) U.S. Cl.
CPC .......... *A61B 8/463* (2013.01); *G06T 7/0016* (2013.01); *G06V 10/761* (2022.01); *G06V 10/765* (2022.01); *G06V 20/41* (2022.01); *G06V 20/46* (2022.01); *G06T 2207/10132* (2013.01); *G06T 2207/30048* (2013.01); *G06T 2207/30056* (2013.01); *G06T 2207/30061* (2013.01)

(58) Field of Classification Search
CPC .......... A61B 8/08; A61B 8/463; A61B 8/465; A61B 8/468; A61B 8/469; A61B 8/485; A61B 8/5223; G06T 2207/10016; G06T 2207/10132; G06T 2207/20076; G06T 2207/20081; G06T 2207/20084; G06T 2207/30048; G06T 2207/30056; G06T 2207/30061; G06T 2207/30084; G06T 2207/30104; G06T 7/0014; G06T 7/0016; G06T 7/269; G06V 10/50; G06V 10/761; G06V 10/765; G06V 20/41; G06V 20/46; G06V 20/47; G06V 2201/031; G16H 30/40
See application file for complete search history.

(56) References Cited

U.S. PATENT DOCUMENTS

2021/0166396 A1* 6/2021 Chen .................... G06T 3/02

* cited by examiner

*Primary Examiner* — Mark D Remaly
(74) *Attorney, Agent, or Firm* — Sheppard Mullin Richter & Hampton LLP

(57) ABSTRACT

Disclosed are a method for displaying ultrasonic data and an ultrasound imaging system. The method may include: acquiring ultrasonic video data to be displayed; obtaining at least one representative frame from the ultrasonic video data; classifying the representative frame to obtain a category of the representative frame, and determining a category of the ultrasonic video data according to the category of the representative frame; and displaying in categories the ultrasonic video data according to the category of the ultrasonic video data.

21 Claims, 5 Drawing Sheets

CLASSIFICATION DISPLAY METHOD OF ULTRASOUND DATA AND ULTRASOUND IMAGING SYSTEM

CROSS REFERENCE TO RELATED APPLICATIONS

This application is based on and claims priority to and benefits of Chinese Patent Application No. 202111272822.1, filed on Oct. 29, 2021. The entire content of the above-identified application is incorporated herein by reference.

TECHNICAL FIELD

The present disclosure relates to ultrasound imaging, and more particularly, to methods for displaying ultrasonic data and ultrasound imaging systems.

BACKGROUND

Available ultrasound devices generally display ultrasound images in chronological order. Doctors can search cases by inputting names, examination IDs, etc. However, all ultrasound images of one same case are simply arranged in chronological order, which fail to meet the use habits of doctors.

In intensive care units (ICUs) and other clinical departments, in order to have a more comprehensive understanding of a patient's condition, a clinician may need to scan different parts at different times to continuously and dynamically evaluate the patient's physiological state and disease progression. For example, where the clinician needs to review all images about the lungs of the patient within a week, and the ultrasound images of each case include the images of other parts in addition to the lung images, the clinician may need to manually open the lung images one by one from the ultrasonic data saved by the ultrasound device and then review and evaluate them. Since the ultrasound images are sorted in chronological order, while the ultrasound images that doctors want to view are not consecutively arranged, operations of continuous viewing and returning are needed during the viewing process, resulting in a time-consuming and cumbersome viewing process.

SUMMARY

A series of concepts in simplified form are introduced in the section of the Summary, which are described in further detail in the section of Detailed Description. The Summary herein is not intended to limit the scope of the present disclosure.

In one embodiment, a method for displaying ultrasonic data is provided, which may include:
acquiring multiple ultrasonic video data to be displayed;
for each ultrasonic video data:
obtaining at least one representative frame from the ultrasonic video data; and
determining a category of the representative frame, and determining a category of the ultrasonic video data according to the category of the representative frame; and
displaying in categories the multiple ultrasonic video data according to the categories of the multiple ultrasonic video data.

In one embodiment, acquiring the multiple ultrasonic video data to be displayed may include:
controlling an ultrasonic probe to transmit ultrasonic waves to a target object and receive ultrasonic echoes of the ultrasonic waves to obtain ultrasonic echo signals; and
performing signal processing on the ultrasonic echo signals to obtain the multiple ultrasonic video data.

In one embodiment, acquiring the multiple ultrasonic video data to be displayed may include obtaining the multiple ultrasonic video data from a memory.

In one embodiment, obtaining at least one representative frame from the ultrasonic video data may include:
obtaining a difference index between adjacent frames according to grayscale distribution information of at least part of the frames in the ultrasonic video data; and
selecting at least one frame as the representative frame according to the difference index between the adjacent frames.

In one embodiment, obtaining a difference index between adjacent frames according to grayscale distribution information of at least part of the frames in the ultrasonic video data may include:
acquiring a grayscale distribution histogram of at least part of the frames in the ultrasonic video data; and
calculating a height or an area of a difference part of the gray distribution histogram between adjacent frames as the difference index between the adjacent frames; and
selecting at least one frame as the representative frame according to the difference index between the adjacent frames may include:
selecting a plurality of consecutive frames with the difference index lower than a first preset threshold, and selecting at least one frame with the smallest variance of the grayscale distribution histogram from the plurality of the consecutive frames as the representative frame.

In one embodiment, obtaining at least one representative frame from the ultrasonic video data may include:
grouping at least part of frames in the ultrasonic video data according to image similarity among the at least part of frames;
determining a center vector of image features in a group of frames with the largest number; and
selecting at least one frame with the closest distance to the center vector of the image features from the group of frames with the largest number of frames as the representative frame.

In one embodiment, grouping at least part of frames in the ultrasonic video data according to image similarity among the frames may include:
grouping a first frame as a first group, and starting from a second frame:
calculating a distance between a current frame and the grouped group, when the distance between the current frame and the grouped group is greater than or equal to a second preset threshold, grouping the current frame as a new group, and when the distance between the current frame and the grouped group is less than the second preset threshold, grouping the current frame into the grouped group with the smallest distance from the current frame.

In one embodiment, obtaining at least one representative frame from the ultrasonic video data may include:
calculating optical flows for at least part of frames in the ultrasonic video data, and obtaining motion vectors of the at least part of frames according to the optical flows;
determining two local maxima in the motion vectors; and
selecting the frame with the smallest motion vector between the two local maxima as the representative frame when a difference between the two local maxima exceeds a third preset threshold.

In one embodiment, obtaining at least one representative frame from the ultrasonic video data may include:

calculating an image similarity between a current frame and a previous representative frame, and determining the current frame as a new representative frame when the image similarity between the current frame and the previous representative frame is greater than a fourth preset threshold.

In one embodiment, obtaining at least one representative frame from the ultrasonic video data may include selecting the first or last frame of the ultrasonic video data as the representative frame.

In one embodiment, determining a category of the representative frame may include determining the category of the representative frame according to a scanning part of the representative frame.

In one embodiment, the scanning part may include a scanning organ, a scanning section or a scanning area.

In one embodiment, determining a category of the representative frame may include determining the category of the representative frame according to an imaging mode of the representative frame.

In one embodiment, determining a category of the representative frame may include:

obtaining image features of the representative frame; and determining the category of the representative frame according to the image features of the representative frame with a preset algorithm.

In one embodiment, the method may further include:

acquiring associated data of the ultrasonic video data, the associated data comprising at least one of: user annotation data, user measurement data, and data representing a type of ultrasonic probe used to acquire the ultrasonic video data;

determining the category of the ultrasonic video data according to the associated data.

In one embodiment, displaying in categories the multiple ultrasonic video data according to the categories of the multiple ultrasonic video data may include:

displaying the ultrasonic video data with a same category in a same display area; or displaying the ultrasonic video data with a same category in a same folder.

In one embodiment, when displaying the ultrasonic video data of a same category in a same folder, the method further may include:

editing the folder according to a user instruction, the editing including at least one of the following: creating a new folder, merging folders, splitting a folder, deleting a folder, and adjusting the sorting of folders.

In one embodiment, the method may further include arranging the ultrasonic video data of a same category in order of examination time.

In one embodiment, the category of the ultrasonic video data comprises a category of the ultrasonic video data determined by a first classification rule and a category of the ultrasonic video data determined by a second classification rule; and displaying in categories the multiple ultrasonic video data according to the categories of the multiple ultrasonic video data comprises: selectively displaying in categories the ultrasonic video data according to the category determined by the first classification rule or according to the category determined by the second classification rule in accordance with a received user instruction.

In one embodiment, selectively displaying in categories the ultrasonic video data according to the category determined by the first classification rule or according to the category determined by the second classification rule in accordance with a received user instruction may include:

when displaying in categories the ultrasonic video data according to the category determined by the first classification rule, switching to displaying in categories the ultrasonic video data according to the category determined by the second classification rule when receiving a user instruction instructing to switch a mode of displaying in categories.

In one embodiment, displaying in categories the multiple ultrasonic video data according to the categories of the multiple ultrasonic video data may include:

displaying a body icon on a display interface, different portions of the body icon corresponding to different scanning parts; and displaying the multiple ultrasonic video data in association with the corresponding portions of the body icon according to the scanning parts of the representative frames of the multiple ultrasonic video data.

In one embodiment, displaying the multiple ultrasonic video data in association with the corresponding portions of the body icon according to the scanning parts of the representative frames of the multiple ultrasonic video data may include displaying identifiers of the multiple ultrasonic video data at different portions of the body icon.

In one embodiment, the method may further include, in response to a selection instruction for the identifier, displaying the ultrasonic video data corresponding to the selected identifier.

In one embodiment, a method for displaying ultrasonic data is provided, which may include:

acquiring multiple ultrasonic data to be displayed, the multiple ultrasonic data including ultrasonic data of different tissue parts;

determining categories of the multiple ultrasonic data at least according to scanning parts of the multiple ultrasonic data;

displaying a body icon on a display interface, different portions of the body icon corresponding to different categories of the multiple ultrasonic data; and displaying the multiple ultrasonic data in association with the corresponding portions of the body icon according to the categories of the multiple ultrasonic data.

In one embodiment, displaying the multiple ultrasonic data in association with the corresponding portions of the body icon according to the categories of the multiple ultrasonic data may include displaying identifiers of the multiple ultrasonic data at different portions of the body icon according to the categories of the multiple ultrasonic data.

In one embodiment, the method may further include, in response to a selection instruction for the identifier, displaying the ultrasonic data corresponding to the selected identifier.

In one embodiment, displaying a body icon on a display interface may include:

displaying a local body icon and a global body icon on the display interface, the size of the local body icon being larger than that of the global body icon;

where the identifiers of the multiple ultrasonic data are displayed on the local body icon, and an icon indicating a relative position of the local body icon in the global body icon is displayed on the global body icon.

In one embodiment, a method for displaying ultrasonic data is provided, which may include:

acquiring multiple ultrasonic data to be displayed, the multiple ultrasonic data including ultrasonic data of different tissue parts;

determining categories of the multiple ultrasonic data; and displaying in categories the ultrasonic data according to the categories of the ultrasonic data, wherein displaying in categories the ultrasonic data may include displaying the ultrasonic data with a same category in a same display area.

In one embodiment, the ultrasonic data with a same category is arranged in order of examination time.

In one embodiment, the categories of the multiple ultrasonic data are determined according to at least one of: scanning part corresponding to the ultrasonic data, imaging mode, type of user annotation item, type of user measurement item, and type of an ultrasonic probe used to acquire the ultrasonic data.

In one embodiment, a method for displaying ultrasonic data is provided, which may include:

acquiring multiple ultrasonic video data to be displayed;

acquiring associated data of the multiple ultrasonic video data; and determining categories of the multiple ultrasonic video data according to representative frames of the multiple ultrasonic video data or the associated data, and displaying in categories the multiple ultrasonic video data.

In one embodiment, an ultrasound imaging system is provided, which may include:

an ultrasonic probe;

a transmitting circuit configured to excite the ultrasonic probe to transmit ultrasonic waves to a target object;

a receiving circuit configured to control the ultrasonic probe to receive echoes of the ultrasonic waves to obtain ultrasonic echo signals;

a display;

a processor configured to:

acquiring multiple ultrasonic video data according to the ultrasonic echo signals;

for each ultrasonic video data:

obtaining at least one representative frame from the ultrasonic video data; and determining a category of the representative frame, and determining a category of the ultrasonic video data according to the category of the representative frame; and controlling the display to display in categories the multiple ultrasonic video data according to the categories of the multiple ultrasonic video data.

BRIEF DESCRIPTION OF THE DRAWINGS

In order to illustrate the technical solutions in the embodiments of the present invention more clearly, the following briefly introduces the accompanying drawings used in the description of the embodiments. Obviously, the accompanying drawings in the following description are only some embodiments of the present invention. For those of ordinary skill in the art, other drawings can also be obtained from these drawings without creative labor.

In the drawings.

DETAILED DESCRIPTION

In order to make the objectives, technical solutions, and advantages of the present application more clear, example embodiments according to the present application will be described in detail below with reference to the accompanying drawings. Apparently, the described embodiments are merely some rather than all of the embodiments of the present application. It should be understood that the example embodiments described herein do not constitute any limitation to the present application. All other embodiments derived by those skilled in the art without creative efforts on the basis of the embodiments of the present application described in the present application shall fall within the scope of protection of the present application.

In the following description, a large number of specific details are given to provide a more thorough understanding of the present application. However, it would be understood by those skilled in the art that the present application can be implemented without one or more of these details. In other examples, to avoid confusion with the present application, some technical features known in the art are not described.

It should be understood that the present application can be implemented in different forms and should not be construed as being limited to the embodiments presented herein. On the contrary, these embodiments are provided to make the disclosure thorough and complete, and to fully convey the scope of the present application to those skilled in the art.

The terms used herein are intended only to describe specific embodiments and do not constitute a limitation to the present application. When used herein, the singular forms of "a", "an", and "said/the" are also intended to include plural forms, unless the context clearly indicates otherwise. It should also be appreciated that the terms "comprise" and/or "include", when used in the specification, determine the existence of described features, integers, steps, operations, elements, and/or units, but do not exclude the existence or addition of one or more other features, integers, steps, operations, elements, units, and/or groups thereof. As used herein, the term "and/or" includes any and all combinations of relevant listed items.

For a thorough understanding of the present application, detailed steps and detailed structures will be provided in the following description to explain the technical solutions proposed by the present application. The preferred embodiments of the present application are described in detail as follows. However, in addition to these detailed descriptions, the present application may further have other implementations.

In the following, an ultrasound imaging system according to an embodiment of the present application is first described with reference to FIG. 1, which shows a schematic structural block diagram of an ultrasound imaging system 100 according to an embodiment of the present application.

Figure 1:
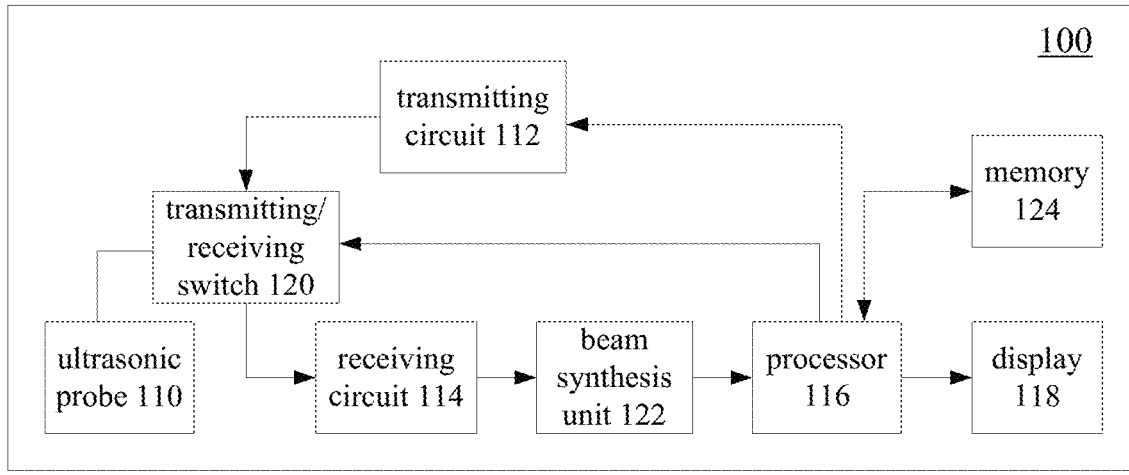
FIG. 1 is a schematic block diagram of an ultrasound imaging system according to an embodiment of the present application.

As shown in FIG. 1, the ultrasound imaging system 100 includes an ultrasonic probe 110, a transmitting circuit 112, a receiving circuit 114, a processor 116 and a display 118.

Further, the ultrasound imaging system may further include a transmitting/receiving switch 120 through which the transmitting circuit 112 and the receiving circuit 114 may be connected to the ultrasonic probe 110, and a beam synthesis unit 122.

The ultrasonic probe 110 may include a plurality of transducer array elements which may be arranged in a row to form a linear array, or in a two-dimensional matrix to form an area array, or in a convex array. The transducers may be configured to transmit ultrasonic waves according to excited electrical signals, or convert received ultrasonic waves into electrical signals; as such, each array element may be configured to mutually convert the electrical pulse signals and the ultrasonic waves, thus realizing transmitting ultrasonic waves to tissues in a target region of a measured object and receiving ultrasonic wave echoes reflected back by the tissues. During ultrasonic testing, it is possible, through a transmission sequence and a reception sequence, to control which transducers for transmitting ultrasonic waves and which transducers for receiving ultrasonic waves, or to control the transducers to transmit ultrasonic waves or receive ultrasonic wave echoes in time slots. The transducers participating in the transmission of the ultrasonic waves may simultaneously be excited by electrical signals to transmit the ultrasonic waves at the same time; or, the transducers participating in the transmission of the ultrasonic waves may also be excited by several electrical signals with a certain time interval to continuously transmit the ultrasonic waves with a certain time interval. In an embodiment, the transducers may be configured to transmit ultrasonic waves that generate an ultrasonic image, and to apply acoustic radiation force pulses to the target region of the measured target to generate shear waves.

During ultrasound imaging, the transmitting circuit 112 may transmit delayed-focused transmission pulses to the ultrasonic probe 110 via the transmitting/receiving switch 120. The ultrasonic probe 110 may be excited by the transmission pulses to transmit ultrasonic waves to the tissues in the target region of the measured object, receive ultrasonic echoes with tissue information reflected from the tissues in the target region after a certain delay, and reconvert the ultrasonic echoes into electrical signals. The receiving circuit 114 may receive the electrical signals converted and generated by the ultrasonic probe 110 to obtain ultrasonic echo signals which are sent to the beam synthesis unit 122. The beam synthesis unit 122 may perform focusing delay, weighting, channel summation and other processing on the ultrasonic echo data, and then send the processed data into the processor 116. The processor 116 may perform signal detection, signal enhancement, data conversion, logarithmic compression and other processing on the ultrasonic echo signals to form an ultrasonic image. Specifically, the processor 116 may perform conventional grayscale imaging processing on the ultrasonic echo signals to generate a grayscale image; or the processor 116 may perform elastic imaging processing on the ultrasonic echo signals to calculate elasticity parameters for generating an elasticity image, so as to generate the corresponding elasticity image according to the elasticity parameters. The ultrasound images obtained by the processor 116 may be displayed on the display 118 or stored in the memory 124.

Alternatively, the processor 116 may be implemented as software, hardware, firmware, or any combination thereof, and may use one or more application specific integrated circuits (ASICs), one or more general-purpose integrated circuits, one or more microprocessors, one or more programmable logic devices, or any combination of the foregoing circuits and/or devices, or other suitable circuits or devices. In addition, the processor 116 may control other components in the ultrasound imaging system 100 to perform corresponding steps of the methods in the various embodiments herein.

The display 118 is connected to the processor 116. The display 118 may be a touch display screen, a liquid crystal display screen or the like; or, the display 118 may be an independent display (such as a liquid crystal display, a TV set, etc.) which is independent of the ultrasound imaging system 100; or, the display 118 may be a display screen of an electronic device such as a smartphone, a tablet or the like. The number of the display 118 may be one or more.

The display 118 may display ultrasound images obtained by the processor 116. In addition, the display 118 may also provide a user with a graphical interface for human-computer interaction while displaying the ultrasound images. The graphical interface may equipped with one or more controlled objects thereon, so that these controlled objects may be controlled by an operating instructions inputted by the user via a human-computer interaction device to perform a corresponding control operation. For example, an icon may be displayed on the graphical interface, and it may be operated by using the human-computer interaction device to perform a specific function.

Optionally, the ultrasound imaging system 100 may also include other human-computer interaction devices other than the display 118, which are connected to the processor 116. For example, the processor 116 may be connected to the human-computer interaction device via an external input/output port. The external input/output port may be a wireless communication unit, a wired communication unit, or a combination of the two. The external input/output port may also be implemented based on USB, bus protocols such as CAN, and/or wired network protocols, and the like.

In this respect, the human-computer interaction device may include an input device for detecting the user's input information. The input information may be, for example, a control instruction for the ultrasonic transmission/reception sequence in time, or may be an operational input instruction for drawing points, lines or boxes on the ultrasonic images, or may include other types of instructions. The input device may include one or more of a keyboard, a mouse, a roller, a trackball, a mobile input device, a multi-function knob, and the like, or a combination thereof. The human-computer interaction device may also include an output device such as a printer.

The ultrasound imaging system 100 may further include a memory 124 for storing instructions executed by the processor, received ultrasound echoes, ultrasound images, and the like. The memory may be a flash memory card, a solid-state memory, a hard disk, or the like. It may be a volatile memory and/or a non-volatile memory, a removable memory and/or a non-removable memory, and the like.

It should be understood that the components included in the ultrasound imaging system 100 shown in FIG. 1 are only schematic, and it may include more or fewer components, which is not limited in the present application.

Figure 2:
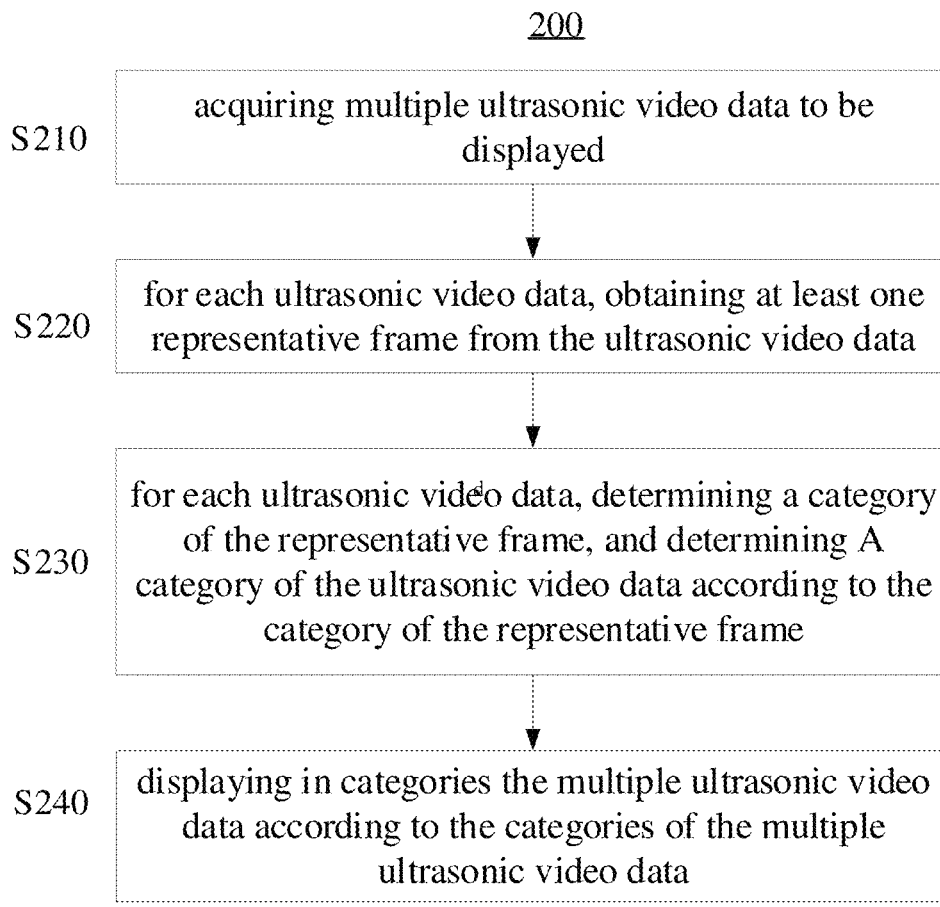
FIG. 2 is a schematic flowchart of a method for displaying ultrasonic data according to an embodiment of the present application.

In the following, a method for displaying ultrasonic data according to an embodiment of the present application is described with reference to FIG. 2. FIG. 2 shows a schematic flowchart of the method 200 for displaying ultrasonic data according to an embodiment of the present application.

As shown in FIG. 2, the method 200 for displaying ultrasonic data according to an embodiment of the present application may include the following steps:

Step 210: acquiring multiple ultrasonic video data to be displayed;

Step 220: for each ultrasonic video data, obtaining at least one representative frame from the ultrasonic video data;

Step 230: for each ultrasonic video data, determining a category of the representative frame, and determining a category of the ultrasonic video data according to the category of the representative frame; and Step 240: displaying in categories the multiple ultrasonic video data according to the categories of the multiple ultrasonic video data.

Specifically, the method 200 for displaying ultrasonic data is used for displaying multiple ultrasonic video data. After classifying the ultrasonic video data according to a representative frame obtained from the ultrasonic video data, the ultrasonic video data is displayed in categories according to the category thereof, which is convenient for users to classify and view the ultrasonic video data, reducing the time required by users to find the ultrasonic video data and improving users' work efficiency.

The ultrasonic video data to be displayed acquired in step 210 may be the ultrasonic video data of a same target object. The ultrasonic video data may be ultrasonic video data collected in real time. Specifically, the ultrasonic probe is controlled to transmit ultrasonic waves to a target object and receive ultrasonic echoes of the ultrasonic waves to acquire ultrasonic echo signals which are processed to obtain ultrasonic video data. Referring to FIG. 1, the ultrasonic probe 110 may be moved by a doctor to choose an appropriate position and angle, receive a group of delayed focused pulses sent by the transmitting circuit 112, and transmit corresponding ultrasonic waves to the target tissue along a corresponding two-dimensional scanning plane. After a certain delay, the receiving circuit 114 may control the transducers in the ultrasonic probe 110 to receive ultrasonic echoes returned by the target tissue. The ultrasonic echoes may be converted into electrical signals to obtain ultrasonic echo signals, and then be transmitted to the beam synthesis unit 122 after signal amplification, analog-to-digital conversion and other processing. The beam synthesis unit 122 may perform corresponding delay and weighted summation processing on the ultrasonic echo signals obtained by multiple transmissions/receptions to realize beamforming, and then send the beamformed ultrasonic echo signals to the processor 116. The processor 116 may perform some or all processing such as logarithmic compression, dynamic range adjustment, digital scan conversion on the ultrasonic echo signals to obtain an ultrasonic image which may be outputted to the display 118 for display. The ultrasonic video data may include a plurality of frames of ultrasonic image data arranged in chronological order.

Exemplarily, there are at least two ways to save the ultrasonic video data collected in real time, one is storage forward and the other is storage backward. The storage forward may refer to taking the ultrasonic video data collected in a preset time range before a current moment as the ultrasonic video data to be displayed. Specifically, during using the ultrasonic probe for ultrasound examination by the doctor, if there is a need to store ultrasonic video data, the ultrasonic probe may be stabilized at a current position, and a save button on a screen or a keyboard may be clicked to save the ultrasonic video data collected within the preset time range before the current time. The preset time may be freely selected by the doctor upon actual situation. When the save button is pressed, the current frame may be taken as the last frame of the ultrasonic video data, and the ultrasonic video data involving the first several seconds in a buffer may be saved. The storage backward may refer to taking the ultrasonic video data collected in a preset time range after the current moment as the ultrasonic video data to be displayed. When the save button is pressed, the current frame may be taken as the first frame of the ultrasonic video data, and the ultrasonic video data involving several seconds thereafter in the buffer may be saved.

In addition, the ultrasonic video data to be displayed may also be pre-stored ultrasonic video data obtained from the memory. The pre-stored ultrasonic video data may be stored after acquiring the ultrasonic video data via the ultrasound imaging system by the doctor, or may be obtained from other devices by the ultrasound imaging system. The ultrasonic video data to be displayed may also be obtained from an external memory.

In step 220, at least one representative frame may be obtained from the ultrasonic video data. The representative frame may be any frame in the ultrasonic video data, including but not limited to the first frame or the last frame. The representative frame may also be a frame that can represent the category of the ultrasonic video data selected from the ultrasonic video data.

For example, a relatively stable clip of frames may be selected from the ultrasonic video data, and one frame of the clip may be selected as the representative frame. Specifically, a difference index between adjacent frames may be obtained according to grayscale distribution information of at least part of the frames in the ultrasonic video data; and at least one frame may be selected as the representative frame according to the difference index between the adjacent frames. In this respect, the grayscale distribution information may be a grayscale distribution histogram, and the obtaining of the difference index between adjacent frames according to the grayscale distribution information may include calculating a height or an area of a difference part of the grayscale distribution histogram between adjacent frames as the difference index between the adjacent frames. The selection of the representative frame according to the difference index may include selecting a plurality of consecutive frames with the difference index lower than a first preset threshold, and selecting at least one frame with the smallest variance of the grayscale distribution histogram among the selected plurality of consecutive frames as the representative frame. The smaller the difference of grayscale histogram, the more stable the ultrasonic probe is, and the more representative frames selected therefrom can represent the entire clip of the ultrasonic video data.

Alternatively, with an algorithm for representative frame extraction based on unsupervised clustering, at least part of the frames in the ultrasonic video data may be grouped according to image similarity between frames, and at least one frame may be selected from a group of frames with the largest number as the representative frame. Specifically, a center vector of image features may be determined in the group of frames with the largest number, and at least one frame with the closest distance to the center vector of the image features may be selected from the group of frames with the largest number as a representative frame. When calculating the distance, a feature vector of each frame that is consistent with the center vector of the whole group of frames in dimension is obtained; then the Euclidean distance between the feature vector of each frame and the center vector may be calculated, and the frame corresponding to the feature vector with the smallest Euclidean distance may be regarded as the representative frame. After the frames are grouped, a group that has the largest number of frames may roughly represent the entire clip of ultrasonic video data, and the frame having the feature vector closest to the center vector in the group may thus be regarded as the representative frame of the entire clip of ultrasonic video data.

Specifically, when grouping the ultrasonic video data, a first frame thereof may be classified as a first group, then starting from a second frame, a distance between a current frame and the established group may be calculated; in this respect, when the distance between the current frame and the established group is greater than or equal to a second preset threshold, the current frame may be classified as a new group, and when the distance between the current frame and the established group is less than the second preset threshold, the current frame may be classified as the established group that has the smallest distance from the current frame. The first frame is not limited to the first frame of the ultrasonic video data in time sequence. For example, the distance between the current frame and the established group may be the distance between the feature vector of the current frame and the center vector of the established group. In another example, the representative frame may be obtained based on motion analysis. Specifically, an optical flow may be first calculated for at least part of the frames in the ultrasonic video data to obtain the motion vector of the frames according to the optical flow; wherein an modular operation may be performed on the sum of the optical flow vectors of each pixel in the frames in two directions as the motion vector of the frames. After that, a motion vector curve may be drawn according to the motion vectors of at least part of the frames, and two local maxima on the motion vector curve may be obtained, and when the difference between the two local maxima exceeds a third preset threshold, the frame with the smallest motion vector between the two local maxima may be used as the representative frame. The smaller the motion vector is, the more stable the ultrasonic probe is. Therefore, the frames collected by the ultrasonic probe in a stable state can be obtained by the above method, and the frames can represent the entire ultrasonic video data.

Alternatively, the representative frame may also be selected based on a tolerance zone method. At least two frames may be obtained from the ultrasonic video data. In an example, a first frame may be chosen as the representative frame, the image similarity between the current frame and a previous representative frame may be calculated; in this connection, when the image similarity between the current frame and the previous representative frame is greater than a fourth preset threshold, the current frame may be determined as the new representative frame. The number of the representative frames obtained by this method may be one or more frames, depending on the fourth preset threshold. The smaller the fourth preset threshold, the greater the number of representative frames. In this respect, incomplete classification of the ultrasonic video data can be avoided by selecting multiple representative frames.

In step 230, the representative frame may be classified to obtain a category of the representative frame, and a category of the ultrasonic video data may be determined according to the category of the representative frame.

In an embodiment, a scanning part of the representative frame may be used as a classification rule to classify the representative frame. The scanning part may include a scanning organ, a scanning section or a scanning area. The scanning organ may include heart, lung, liver, kidney, and other organs; the scanning section may include a standard or non-standard section such as an apical four chamber view and a parasternal long axis view; and the scanning area may include area like head and abdomen. Further, each scanning area may include multiple organs. The scanning part of the representative frame is the scanning part of the ultrasonic video data. After the scanning part of the ultrasonic video data is determined, the ultrasonic video data can be displayed in categories according to the scanning part thereof, so that when the ultrasonic video data of a specific scanning part is needed to be viewed by the user, there is no need to find it one by one in a large number of ultrasonic video data, thus improving work efficiency.

Exemplarily, deep learning or machine learning may be used to classify the scanning parts of the representative frame, that is, the image features of the representative frame may be first obtained, and then the obtained image features may be classified by using a preset algorithm to obtain the scanning parts corresponding to the representative frame.

In this respect, when using the deep learning method to classify the scanning part of the representative frame, a neural network needs to be constructed first. The neural network may consist of stacks of a convolutional layer, a pooling layer, and a fully connected layer. In the convolution layer, image features may be obtained by performing a convolution operation on the image in a sliding manner with a convolution kernel. Feature extraction networks may include lexNet, VGG, Inception, ResNet, DenseNet, etc., as well as lightweight networks such as MobileNet series and ShuffleNet series. In the pooling layer, the dimension of a feature map obtained by the convolutional layer may be reduced to obtain features that are more representative; then with the fully connected layer or a global average pooling layer, a feature vector that can represent the scanning part may be obtained; and finally, the feature vector may be classified by a classification algorithm such as a softmax function to obtain the category of the scanning part.

In order to obtain a neural network capable of classifying scanning parts, it is necessary to train and test the neural network in advance. A training set may need to be built during training. The training set may contain multiple categories of different scanning parts, and each category of each scanning part may contain training images of a plurality of cases. The training images may have labels corresponding to the categories. By means of inputting these labeled training images to the neural network, and adjusting the parameters of the neural network iteratively, the probability of the category to which the training images belong can be correctly output by the neural network. During testing, a new ultrasound image of a different scanning part is inputted, and, with the previously trained neural network, the new image can be predicted which scanning part it may be belong to; in this connection, the scanning part of the representative frame can be predicted by the tested neural network.

As for classification methods based on machine learning, the primary concept thereof is to extract the image features of the representative frame by traditional methods such as PCA, LDA, HOG, Harr, and LBP, and classify the image features using classification algorithms such as KNN, SVM and decision tree, thereby obtaining the scanning part of the representative frame. The principle of the KNN classification algorithm is to calculate a distance between the image features of the representative frame and the image features of the training image (such as Euclidean distance, Hamming distance, etc.), and select several training images with the smallest distance to the representative frame, wherein the category of the training images with the largest number of occurrences is regarded as the category of the representative frame. The SVM classification algorithm is mainly used for binary classification; that is, a hyperplane is trained using the training set, wherein a representative frame belonging to the category of the training set is divided into one side of the hyperplane, and a representative frame that does not belong to the category of the training set is divided into the other side of the hyperplane. When a representative frame is input to the SVM classification algorithm, it may be determined whether it belongs to the category of the training set corresponding to the SVM classification algorithm by the classification algorithm; in this respect, multiple categories can be classified by using multiple SVM classification algorithms. The decision tree is used to simulate the process of human decision-making in the form of a binary tree or a multi-branch tree, wherein a tree model is established for each category of the training set, and each node of the tree corresponds to a feature. When the representative frame is inputted, the decision tree may determine the scanning part of the representative frame according to whether the representative frame contains the feature.

In addition to the scanning part, the imaging mode of the representative frame may also be adopted as a classification rule to classify the representative frame. The imaging mode may include grayscale imaging mode, elastic imaging mode, color blood flow imaging mode and so on; and ultrasound images in different imaging modes may have different image features. The imaging mode of the representative frame is the imaging mode of the ultrasonic video data containing the representative frame. The way to determine the imaging mode of the representative frame is similar to the way to determine the scanning part of the representative frame, that is, the method of deep learning or machine learning is adopted to first extract the image features of the representative frame, and then classify the obtained image features using a classification algorithm to obtain the imaging mode of the representative frame. Exemplarily, if there is a flag bit representing the imaging mode in the ultrasonic video data, the imaging mode of the ultrasonic video data may be directly determined according to the flag bit.

After obtaining the category of the representative frame, the category of the representative frame may be directly served as the category of the ultrasonic video data. In addition to classifying the ultrasonic video data based on the representative frame, data associated to the ultrasonic video data may also be acquired, and the category of the ultrasonic video data may be determined upon the associated data. The category of the ultrasonic video data may include a category determined upon the representative frame and a category determined upon the associated data.

Exemplarily, the associated data may include at least one of the following: user annotation data, user measurement data, and data representing the type of an ultrasonic probe used to acquire the ultrasonic video data. For example, given that "L" indicates the left side and "R" indicates the right side, then the ultrasonic video data annotated with "L" is classified as one category, and the ultrasonic video data annotated with "R" is classified as another category. When classifying according to the user measurement data, the ultrasonic video data involving measuring area may be classified as one category, and the ultrasonic video data involving measuring length may be classified as another category. When classifying according to the type of the ultrasonic probe, the ultrasonic video data collected by a linear array probe may be classified as one category, the ultrasonic video data collected by a convex array probe may be classified as another category, and the ultrasonic video data collected by a phased array probe may be classified as yet another category.

Exemplarily, after determining the category of the ultrasonic video data, the ultrasonic video data may also be stored in categories according to the category of the ultrasonic video data, so as to facilitate subsequent retrieval of the ultrasonic video data of different categories.

Then, in step S240, the ultrasonic video data is displayed in categories according to the category of the ultrasonic video data. The display in categories enables doctors to view all ultrasonic video data of a same category at one time, reducing the time for doctors to choose the ultrasonic video data.

Figure 3:
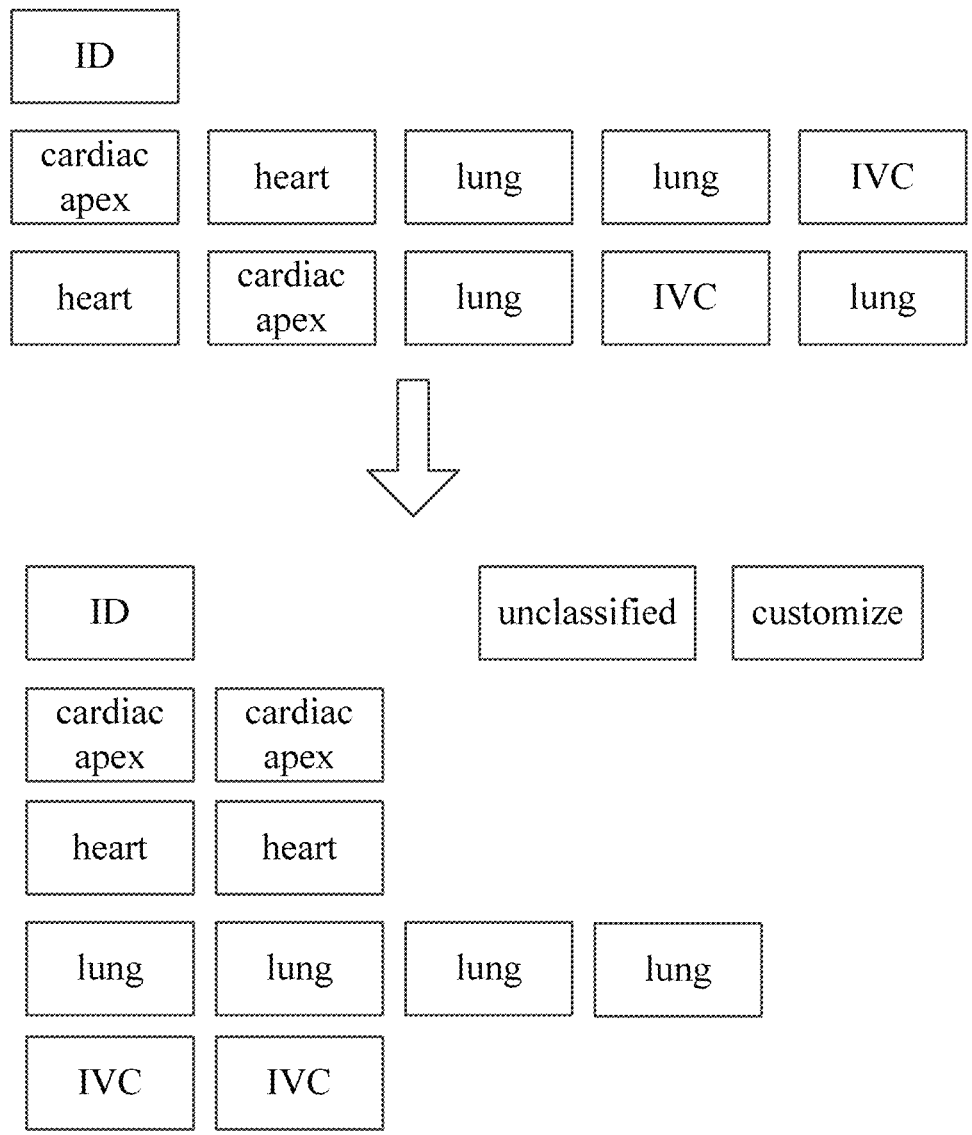
FIG. 3 is a schematic diagram of a classification and display mode according to an embodiment of the present application.

In one embodiment, the display in categories may be implemented in a specific way that displays the ultrasonic video data corresponding to a same category in the same display area in a display interface. The same display area may have various forms, such as a same row, a same column, or a same matrix. Correspondingly, the ultrasonic video data of different categories may be displayed in different display areas of the display interface. Referring to FIG. 3, there is shown a comparison diagram of a non-classified display mode and a classified display mode based on the scanning part. When adopting the non-classified display mode, all the ultrasonic video data may be arranged in order of examination time; and when the user needs to view the ultrasonic video data about a patient's heart, all the ultrasonic video data may need to be viewed and filtered one by one. While the classified display mode is adopted, the ultrasonic video data may be classified and displayed according to the scanning part, and the ultrasonic video data of a same line corresponds to the same scanning part, saving the user's time for screening.

In another embodiment, the ultrasonic video data corresponding to a same category may also be displayed in a same folder. Exemplarily, the folder may be named after the category of ultrasonic video data, or a graphic capable of representing the ultrasonic video data may be adopted as an icon of the folder to represent the category of the ultrasonic video data in the folder. Further, the folder may be edited according to a user instruction, wherein the editing may include at least one of the following: creating a folder, merging folders, splitting a folder, deleting a folder, and adjusting the sorting of folders. For example, an edit mode may be entered by touching and holding a folder or other ways by a doctor; in this connection, all folders may be edited in the edit mode, including dragging a folder to merge or split multiple folders, dragging a folder according to the doctor's needs to change the sorting order among folders, or deleting the entire folder.

In addition, a new folder can be created by the doctor. For example, a new folder named "typical cases" can be created to store ultrasonic data of typical cases of interest by the doctor during browsing the ultrasound data; for another example, a new folder named "wrong" can be created by the doctor to store misclassified ultrasonic data.

In yet another embodiment, when the category of the ultrasonic video data includes the scanning part of the ultrasonic video data, a body icon may be displayed on the display interface, and different portions of the body icon correspond to different scanning parts; simultaneously, according to the scanning part of the ultrasonic video data, the ultrasonic video data is displayed in association with corresponding point of the body icon.

Figure 4A:
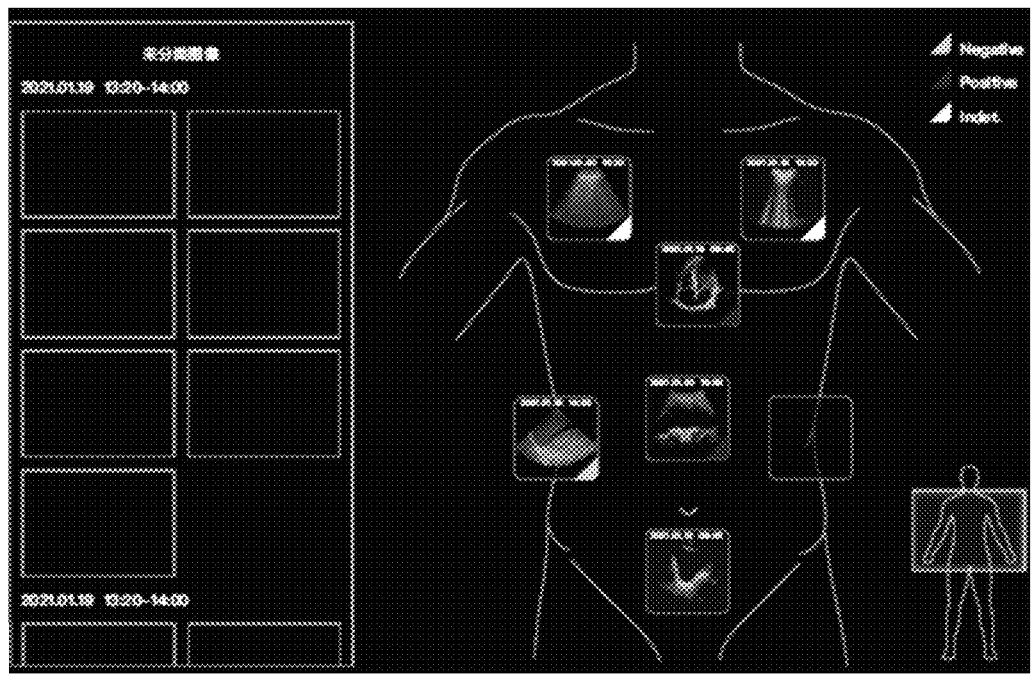
FIG. 4A and FIG. 4B are schematic diagrams of a classification and display mode according to another embodiment of the present application respectively.
Figure 4B:
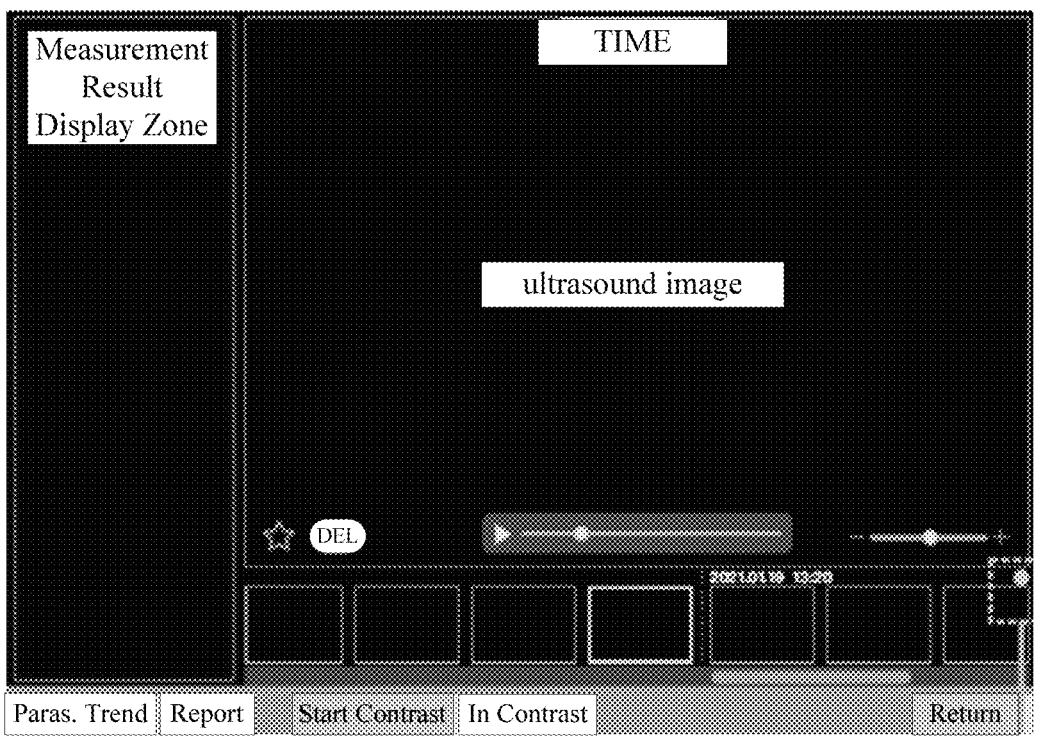

Referring to FIG. 4A and FIG. 4B. As shown in FIG. 4A, identifiers of the ultrasonic data are displayed at different portions of the body icon, and each individual identifier of the ultrasonic video data may be a small image of any frame of the ultrasonic video data. When a selection instruction for the identifier is acquired, the ultrasonic video data corresponding to the scanning part is displayed according to the scanning part corresponding to the identifier. For example, referring to FIG. 4A, the body icon may include a local body icon displayed in the center of the display interface and a global body icon displayed in the lower right corner of the display interface. The local body icon configured to represent different scanning parts may have a size larger than the size of the global body icon. The identifier of the ultrasonic image data is displayed on the local body icon, and an icon indicating a relative position of the local body icon in the global body icon is displayed on the global body icon. The icon shown in FIG. 4A is a rectangular box that selects the location of the local body icon. When the scanning part covered by the local body icon can be changed by moving the mouse up and down or touching the screen by the user, for example, the local body icon shown in FIG. 4A covers the upper limbs of the human body, and it can be adjusted by the user to be moved upward to cover the head of the human body or to be moved downward to cover the lower limbs of the human body.

When the identifier of the ultrasonic video data displayed on the local body icon is clicked by the user, the ultrasonic video data of the scanning part corresponding to the identifier can be displayed. For example, when the user clicks an expansion icon of the ultrasound image at the lower right corner displayed at the location of the heart, one or more segments of ultrasonic video data involving the scanning part being the heart can be displayed.

In one embodiment, the body icon is displayed on a first display interface, and the ultrasonic video data is displayed on a second display interface. When the identifier of the ultrasonic video data on the body icon in the first display interface is clicked by the user, it may switch to the second display interface to display the ultrasonic video data corresponding to the scanning part in an enlarged manner. On the second display interface, all the ultrasonic video data corresponding to the scanning part can be displayed side by side, or a small image of the ultrasonic video data can be displayed at the bottom of the interface and an enlarged image of the ultrasonic video data can be displayed at the top of the interface to facilitate users to view the details of the ultrasonic video data.

Exemplarily, the category of the ultrasonic video data includes a category of the ultrasonic video data determined by a first classification rule and a category of the ultrasonic video data determined by a second classification rule; when displaying in categories the ultrasonic video data according to the category of the ultrasonic video data, in accordance with a received user instruction, the ultrasonic video data is selectively to be displayed in categories according to the category determined by the first classification rule or according to the category determined by the second classification rule. For example, when the first classification rule is the scanning part of the ultrasonic video data and the second classification rule is the imaging mode of the ultrasonic video data, it is possible to, in accordance with the user instruction, switch between the display in categories of the ultrasonic video data according to the scanning part and the display in categories of the ultrasonic video data according to the imaging mode.

Exemplarily, when displaying in categories the ultrasonic video data according to the category determined by the first classification rule, switching to display in categories the ultrasonic video data according to the category determined by the second classification rule when receiving a user instruction to switch the mode of display in categories. The first classification rule may be a default classification rule. If the user is not satisfied with the default classification rule, the user may switch the display in categories the ultrasonic video data according to other classification rules. Of course, after switching to display in categories the ultrasonic video data according to the category determined by the second classification rule, it may also be switched to, according to the received user instruction, display in categories the ultrasonic video data according to the category determined by the first classification rule. Referring to FIG. 3, the user can also click an "unclassified" icon in the upper right corner to cancel the display in categories, or click a "customize" icon to customize the display mode.

While the ultrasonic video data is displayed in categories according to the category of ultrasonic video data, the ultrasonic video data of the same category can also be arranged in order of examination time. For example, when the ultrasonic video data corresponding to the same category is displayed in the same display area of the display interface, the ultrasonic video data corresponding to the same scanning part in the same display area can also be arranged in order of examination time; or, when the ultrasonic video data corresponding to the same category is displayed in the same folder, it is also possible to arrange multiple segments of the ultrasonic video data in the same folder in order of examination time.

In conclusion, with the method 200 for displaying ultrasonic data according to the embodiment of the present application, after classifying the ultrasonic video data according to the representative frame obtained from the ultrasonic video data, the ultrasonic video data can be displayed in categories according to the category thereof, facilitating users to review the ultrasonic data in categories, reducing the time required for users to search for the ultrasonic data, and improving users' work efficiency.

Figure 5:
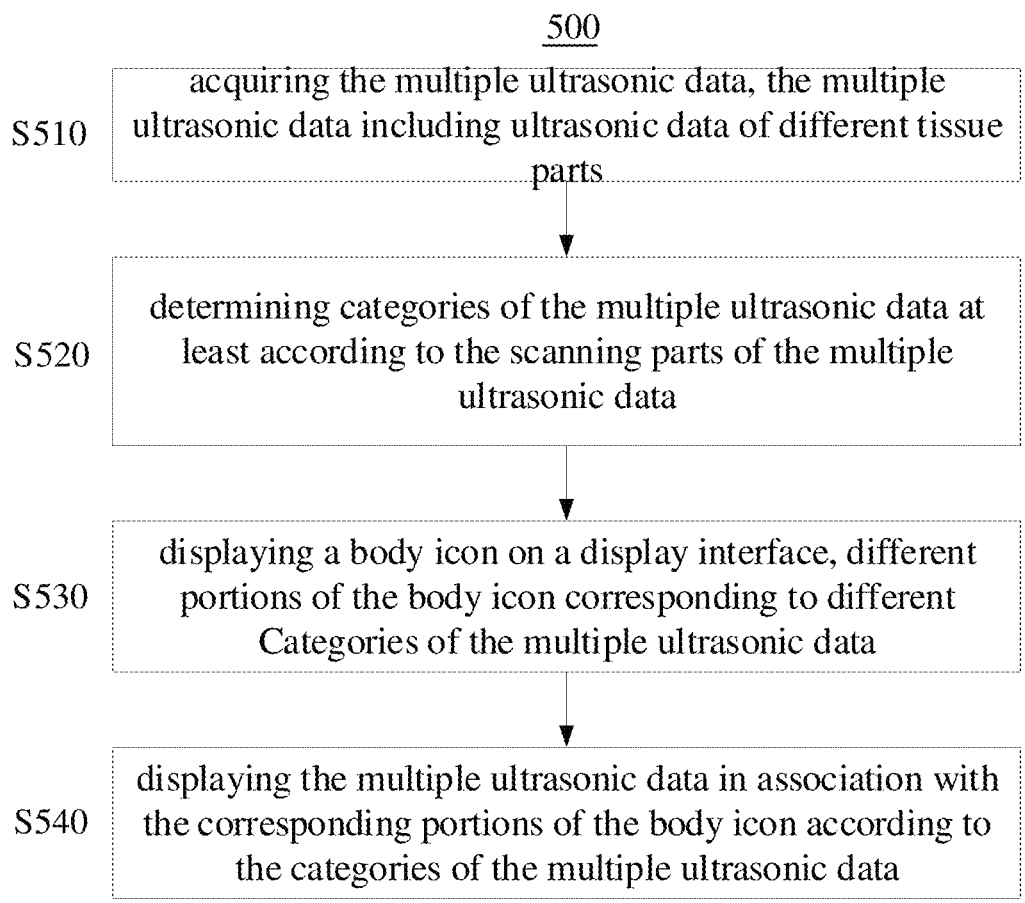
FIG. 5 is a schematic flowchart of a method for displaying ultrasonic data according to another embodiment of the present application.

Referring to FIG. 5, a method 500 for displaying ultrasound data provided in accordance with another embodiment of the present application may include:

step S510: acquiring the multiple ultrasonic data to be displayed, the multiple ultrasonic data including ultrasonic data of different tissue parts;

step S520: determining the categories of the multiple ultrasonic data at least according to the scanning parts of the multiple ultrasonic data;

step S530: displaying a body icon (such as a human body icon or an animal body icon, etc.) on a display interface, different portions of the body icon corresponding to different scanning parts; and step S540: displaying the multiple ultrasonic data in association with the corresponding portions of the body icon according to the categories of the multiple ultrasonic data.

The method 500 for displaying ultrasound data in this embodiment of the present application is used for displaying the ultrasound data in categories, including dynamic ultrasonic video data or static ultrasound image data. When displaying in categories, the ultrasonic data is displayed in association with the corresponding portions of the body icon so as to facilitate the user to view the ultrasonic data of different scanning parts. The ultrasonic data including ultrasonic data of different tissue parts can be ultrasound data obtained in scenarios such as ICU where patients need to be examined thoroughly; in this connection, the ultrasonic data usually includes different tissue parts. For the ultrasonic data including different tissue parts, the category thereof can be illustrated more clearly in combination with the body icon.

In this embodiment, if the ultrasonic data to be displayed is ultrasonic video data, in addition to classifying the ultrasonic video data based on the representative frame, the ultrasonic video data can also be directly inputted into a classification algorithm to obtain a classification result.

For example, three-dimensional spatial and temporal features can be obtained by deep learning methods, that is, first using CNN, RNN, 3D full convolution network, LSTM and other deep neural networks to extract two-dimensional spatial features and temporal features from ultrasonic video data. For example, image features may be obtained from a single frame by using CNN, and then the obtained image features may be integrated in temporal dimension by using RNN network. Alternatively, 3D convolution kernels may be directly used to extract image features from frames, and to model motion sequences among adjacent frames. Alternatively, CNN is used for feature extraction of frames, and then optical flow images are used to extract temporal dimension features. Alternatively, two-dimensional CNN is used to extract the features of the scanning part frame by frame, and then LSTM network is used to model the features obtained by the two-dimensional CNN in temporal dimension. After the extraction of 3D features is completed, the obtained features may be inputted into a classification function to directly acquire the ultrasonic video data.

In addition to deep learning methods, the ultrasonic video data can also be classified by traditional image processing methods; for example, 3D Harris corner detection operator, computational optical flow, 3D SIFT operator and other algorithms may be used to extract features of spatial and temporal dimensions, including HOG, HOF, MBH and other features, and then classification algorithms such as SVM may be adopted to classify to obtain the category of ultrasonic video data.

If the ultrasonic data to be displayed is two-dimensional ultrasonic image data, the classification method thereof is similar to that of the representative frame of the ultrasonic video data. For details, please refer to the above.

After the scanning part of the ultrasound data is determined, the ultrasonic data is displayed in association with the corresponding portions of the body icon according to the scanning part of the ultrasonic data, referring to FIG. 4A and FIG. 4B. The scanning part of an ultrasound image is the tissue part corresponding to the ultrasound image. Specifically, an identifier of the ultrasonic data is displayed at different portions of the body icon, the identifier of the ultrasound data can be a small map of any frame of ultrasound data; and when a selection instruction for the identifier is acquired, the ultrasonic data corresponding to the scanning part is displayed according to the scanning part corresponding to the identifier.

Exemplarily, displaying a body icon on a display interface may comprise: displaying a local body icon and a global body icon on the display interface, the size of the local body icon being larger than that of the global body icon; wherein the identifier of the ultrasonic image data is displayed on the local body icon, and an icon indicating a relative position of the local body icon in the global body icon is displayed on the global body icon. The display of the enlarged local body icon is helpful for users to distinguish different scanning parts.

In one embodiment, the body icon is displayed on a first display interface, and the ultrasonic data is displayed on a second display interface. When the identifier of the ultrasonic data on the body icon in the first display interface is clicked by the user, it may switch to the second display interface to display the ultrasonic data corresponding to the scanning part in an enlarged manner. On the second display interface, all the ultrasonic data corresponding to the scanning part can be displayed side by side, or a small image of the ultrasonic data can be displayed at the bottom of the interface and an enlarged image of the ultrasonic data can be displayed at the top of the interface to facilitate users to view the details of the ultrasonic data.

For other specific details of the method 500 for displaying ultrasound data, reference may be made to the relevant description in the method 200 for displaying ultrasound data, which will not be repeated here.

With the method 500 for displaying ultrasonic data according to the embodiment of the present application, after classifying the ultrasonic data, according to the body icon, the ultrasonic data can be displayed in categories according to the scanning part of the ultrasonic data, facilitating users to review the ultrasonic data in categories, reducing the time required for users to search for the ultrasonic data, and improving users' work efficiency.

Figure 6:
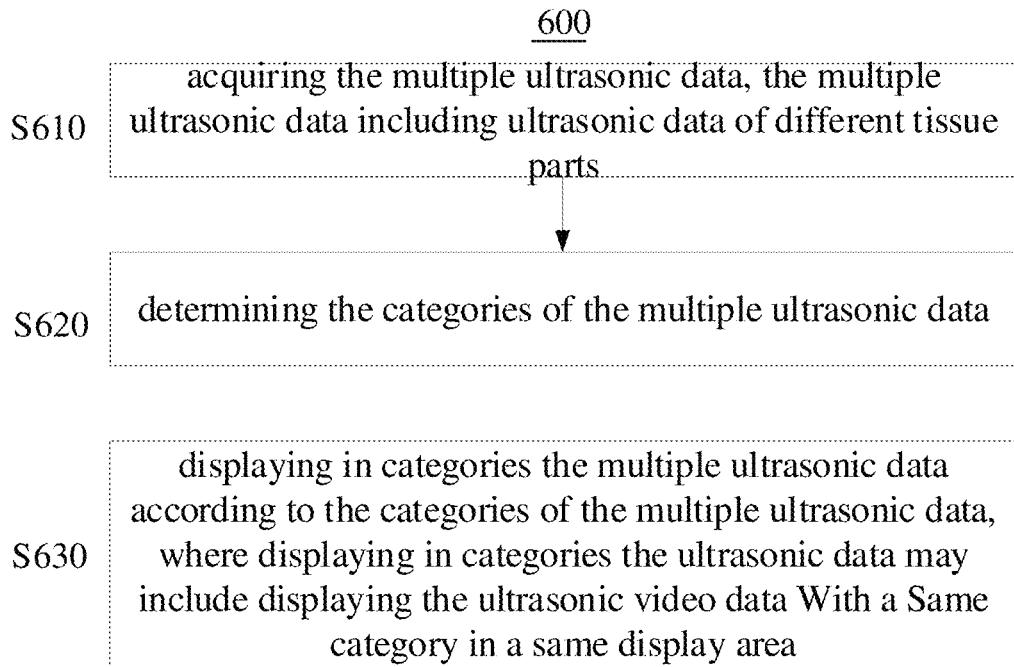
FIG. 6 is a schematic flowchart of a method for displaying ultrasonic data according to yet another embodiment of the present application.

Referring to FIG. 6, a method 600 for displaying ultrasound data provided in accordance with yet another embodiment of the present application may include:

step S610: acquiring the multiple ultrasonic data to be displayed, the multiple ultrasonic data including ultrasonic data of different tissue parts;

step S620: determining the categories of the ultrasonic data; and step S630: displaying in categories the ultrasonic data according to the categories of the ultrasonic data, where displaying in categories the ultrasonic data may include displaying the ultrasonic video data with a same category in a same display area.

The method 600 for displaying ultrasound data in this embodiment of the present application is used for displaying in categories the ultrasound data, including dynamic ultrasonic video data or static ultrasound image data. When displaying in categories, the ultrasound data corresponding to the same category is displayed in the same display area, and the ultrasound data corresponding to different categories is displayed in different display areas. The same display area may refer to the same row, the same column, the same matrix, and so on. The ultrasonic data including ultrasonic data of different tissue parts can be ultrasound data obtained in scenarios such as ICU where patients need to be examined thoroughly; in this connection, the ultrasonic data usually includes different tissue parts. For the ultrasonic data including different tissue parts, the category thereof can be illustrated more clear by displaying the ultrasonic data corresponding to the same category in the same display area.

In an embodiment, the ultrasonic data corresponding to a same category is arranged in order of examination time when displaying he ultrasonic data corresponding to the same category. For example, if the ultrasound data of the same category are displayed in the same row, the different ultrasound data displayed in the same row are arranged in order of examination time.

In an embodiment, the category of the ultrasonic data may comprise at least one of the following: scanning part corresponding to the ultrasonic data, imaging mode, type of user annotation item, type of user measurement item, and type of an ultrasonic probe used to acquire the ultrasonic data. The specific method for classifying ultrasound data can refer to the relevant description in the method 200 for displaying ultrasound data, and will not be described here.

With the method 600 for displaying ultrasonic data according to the embodiments of the present application, after the ultrasonic data is classified, it can be displayed in categories, facilitating users to review in categories the ultrasonic data, reducing the time required for users to search for the ultrasonic data, and improving users' work efficiency.

Figure 7:
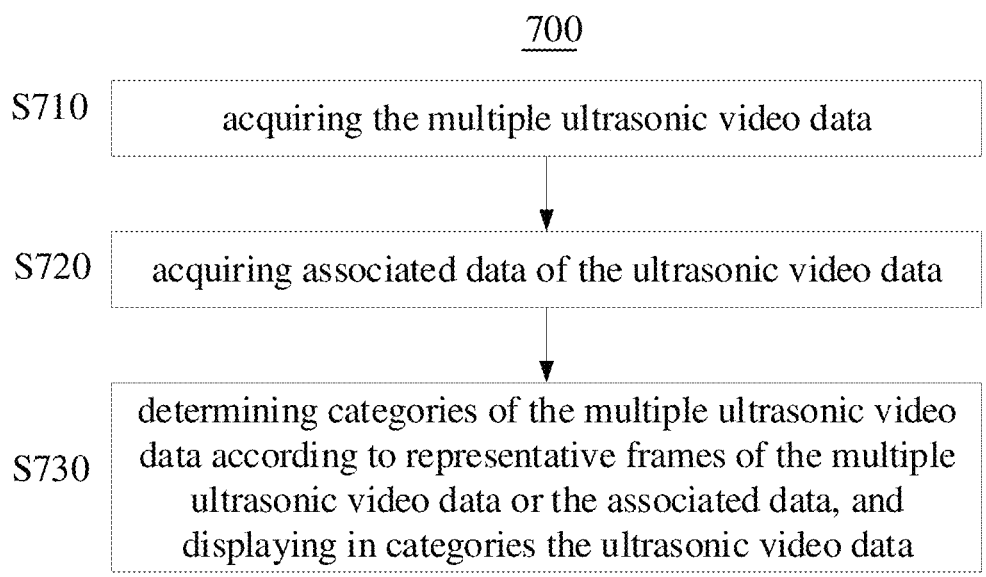
FIG. 7 is a schematic flowchart of a method for displaying ultrasonic data according to yet another embodiment of the present application.

Referring to FIG. 7, a method 700 for displaying ultrasound data provided in accordance with yet another embodiment of the present application may include:

step S710: acquiring multiple ultrasonic video data to be displayed;

step S720: acquiring associated data of the multiple ultrasonic video data; and step S730: determining the categories of the multiple ultrasonic video data according to representative frames of the multiple ultrasonic video data or the associated data, and displaying in categories the multiple ultrasonic video data.

The method 700 for displaying ultrasonic data according to this embodiment is generally similar to the method 200 for displaying ultrasonic data described above, except that in the method 700 for displaying ultrasonic data, the category of ultrasonic video data can be determined according to the representative frame of the ultrasonic video data, or be determined according to the associated data of the ultrasonic video data. For example, after obtaining the associated data, the associated data is first identified; if it is identified that the associated data contains the user's annotation on the scanning part, there is no need to extract the representative frame of the ultrasonic video data to classify the scanning part of the ultrasonic video data. A specific way to classify the ultrasonic video data according to the associated data or the representative frame may be implemented by referring to the relevant description in the method 200 for displaying ultrasonic data, and details are not described here.

Referring again to FIG. 1, an ultrasound imaging system 100 may further be provided according to an embodiment of the present disclosure. The ultrasound imaging system 100 can be used to implement the method 200 for displaying ultrasound data, the method 500 for displaying ultrasound data, the method 600 for displaying ultrasound data and the method 700 for displaying ultrasound data mentioned above. The ultrasound imaging system 100 may include part or all components of the ultrasonic probe 110, the transmitting circuit 112, the receiving circuit 114, the processor 116, the display 118, the transmitting/receiving switch 120, the beam synthesis unit 122 and the memory 124, and relevant description of each component may refer to the above. Only the main functions of the ultrasound imaging system 100 will be described below, and the details already described above will be omitted.

When used to implement the method 200 for displaying ultrasonic data, the transmitting circuit 112 is configured to excite the ultrasonic probe 110 to transmit ultrasonic waves to a target tissue; the receiving circuit 114 is configured to control the ultrasonic probe 110 to receive the ultrasonic echoes returned from the target tissue to obtain ultrasonic echo signals; and the processor 116 is configured to: acquire ultrasonic video data to be displayed; extract at least one representative frame from the ultrasonic video data; classify the representative frame to obtain a category of the representative frame, and determine a category of the ultrasonic video data according to the class corresponding to the representative frame; and control the display 118 to display the classified ultrasonic video data according to the category of the ultrasonic video data.

When used to implement the method 500 for displaying ultrasonic data, the transmitting circuit 112 is configured to excite the ultrasonic probe 110 to transmit ultrasonic waves to a target tissue; the receiving circuit 114 is configured to control the ultrasonic probe 110 to receive the ultrasonic echoes returned from the target tissue to obtain ultrasonic echo signals; and the processor 116 is configured to: acquire the ultrasonic data to be displayed; classify the ultrasonic data to obtain a category of the ultrasonic data that at least includes a scanning part of the ultrasonic data; control the display 118 to display a body icon on a display interface, different portions of the body icon corresponding to different scanning parts; display the ultrasonic data in association with the corresponding portions of the body icon according to the scanning part of the ultrasonic data; and control the display 118 to display the ultrasonic data in association with the corresponding portions of the body icon.

When used to implement the method 600 for displaying ultrasonic data, the transmitting circuit 112 is configured to excite the ultrasonic probe 110 to transmit ultrasonic waves to a target tissue; the receiving circuit 114 is configured to control the ultrasonic probe 110 to receive the ultrasonic echoes returned from the target tissue to obtain ultrasonic echo signals; the processor 116 is configured to: acquire ultrasonic data to be displayed; classify the ultrasonic data to obtain a category of the ultrasonic data; and control the display 118 to classify and display the ultrasonic data according to the category of the ultrasonic data, wherein the displaying in categories may include displaying the ultrasonic data corresponding to a same category in a same display area.

When used to implement the method 700 for displaying ultrasonic data, the transmitting circuit 112 is configured to excite the ultrasonic probe 110 to transmit ultrasonic waves to a target tissue; the receiving circuit 114 is configured to control the ultrasonic probe 110 to receive the ultrasonic echoes returned from the target tissue to obtain ultrasonic echo signals; the processor 116 is configured to: acquire ultrasonic video data to be displayed; acquire associated data of the ultrasonic video data; and determine a category of the ultrasonic video data according to a representative frame of the ultrasonic video data or the associated data, and control the display 118 to classify and display the ultrasonic video data.

With the methods for displaying ultrasonic data and ultrasound imaging systems according to the embodiments of the present application, the ultrasonic data is displayed in categories according to the category thereof, facilitating users to review in categories the ultrasonic data, reducing the time required for users to search for the ultrasonic data, and improving users' work efficiency.

While exemplary embodiments have been described herein with reference to the accompanying drawings, it should be understood that the above example embodiments are merely illustrative and are not intended to limit the scope of the disclosure thereto. Those skilled in the art may make various changes and modifications therein without departing from the scope and spirit of the disclosure. All such changes and modifications are intended to be included in the scope of the disclosure as claimed in the appended claims.

A person of ordinary skill in the art may be aware that, in combination with the examples described in the embodiments disclosed in this specification, units and algorithm steps may be implemented by using electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present disclosure, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this specification provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention, namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or devices as disclosed. Unless explicitly stated otherwise, each feature disclosed in this specification (along with the appended claims, abstract, and drawings) may be replaced by an alternative feature that provides the same, equivalent, or similar object.

Furthermore, those skilled in the art should understand that although some of the embodiments described herein comprise some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The word "comprising" does not exclude the presence of elements or steps not listed in a claim. The word "a" or "an" preceding an element does not exclude the presence of a plurality of such elements. The disclosure may be implemented by means of hardware comprising several different elements and by means of an appropriately programmed computer. In unit claims listing several ultrasound devices, several of these ultrasound devices may be specifically embodied by one and the same item of hardware. The use of the terms "first", "second", "third", etc. does not indicate any order. These terms may be interpreted as names.

The above is only the specific embodiment of the present disclosure or the description of the specific embodiment, and the protection scope of the present disclosure is not limited thereto. Any changes or substitutions should be included within the protection scope of the present disclosure. The protection scope of the present disclosure shall be subject to the protection scope of the claims.

What is claimed is:

1. A method for displaying ultrasonic data, comprising:
acquiring multiple ultrasonic video data to be displayed;
obtaining a representative frame from each ultrasonic video data;
determining a category of each representative frame;
determining a category of each ultrasonic video data according to the category of the representative frame obtained from said ultrasonic video data; and
displaying in categories the multiple ultrasonic video data according to the respective category determined for each ultrasonic video data.

2. The method according to claim 1, wherein obtaining the representative frame from each ultrasonic video data comprises:
calculating a difference index between adjacent frames according to grayscale distribution information of at least part of frames in the ultrasonic video data; and
selecting one frame as the representative frame according to the difference index between the adjacent frames.

3. The method according to claim 2, wherein,
calculating the difference index between the adjacent frames according to the grayscale distribution information of at least part of the frames in the ultrasonic video data comprises:
acquiring a grayscale distribution histogram of at least part of the frames in the ultrasonic video data; and
calculating a height or an area of a difference part of the gray distribution histogram between adjacent frames as the difference index between the adjacent frames; and
selecting one frame as the representative frame according to the difference index between the adjacent frames comprises:
selecting a plurality of consecutive frames with the difference index lower than a first preset threshold, and selecting one frame with a smallest variance of the grayscale distribution histogram from the plurality of the consecutive frames as the representative frame.

4. The method according to claim 1, wherein obtaining the representative frame from each ultrasonic video data comprises:
grouping at least part of frames in the ultrasonic video data according to image similarity among the at least part of frames to obtain a plurality of groups of frames;
determining a center vector of image features of frames in a group of frames with a largest number of frames among the plurality of groups of the frames; and
selecting one frame with a closest distance to the center vector of the image features from the group of frames with the largest number of frames as the representative frame.

5. The method according to claim 4, wherein grouping at least part of frames in the ultrasonic video data according to the image similarity among the at least part of frames comprises:
grouping a first frame into a first group, and starting from a second frame:
calculating a distance between a current frame and the grouped group, when the distance between the current frame and the grouped group is greater than or equal to a second preset threshold, grouping the current frame into a new group, and when the distance between the current frame and the grouped group is less than the second preset threshold, grouping the current frame into the grouped group with a smallest distance from the current frame.

6. The method according to claim 1, wherein obtaining the representative frame from each ultrasonic video data comprises:
calculating optical flows for at least part of frames in the ultrasonic video data, and obtaining motion vectors of the at least part of frames according to the optical flows;
determining two local maxima in the motion vectors; and
selecting the frame with a smallest motion vector between the two local maxima as the representative frame when a difference between the two local maxima exceeds a third preset threshold.

7. The method according to claim 1, wherein obtaining the representative frame from each ultrasonic video data comprises:
calculating an image similarity between a current frame and a previous representative frame, and determining the current frame as a new representative frame when the image similarity between the current frame and the previous representative frame is greater than a fourth preset threshold.

8. The method according to claim 1, wherein obtaining the representative frame from each ultrasonic video data comprises:
selecting a first or a last frame of the ultrasonic video data as the representative frame.

9. The method according to claim 1, wherein determining the category of each representative frame comprises:
determining the category of the representative frame according to a scanning part of the representative frame.

10. The method according to claim 1, wherein determining the category of each representative frame comprises:
determining the category of the representative frame according to an imaging mode of the representative frame.

11. The method according to claim 1, wherein determining the category of each representative frame comprises:
obtaining image features of the representative frame; and
determining the category of the representative frame according to the image features of the representative frame with a preset algorithm.

12. The method according to claim 1, further comprising:
acquiring associated data of each ultrasonic video data, the associated data comprising at least one of: user annotation data, user measurement data, and data representing a type of ultrasonic probe used to acquire the ultrasonic video data; and
determining the category of each ultrasonic video data according to the associated data.

13. The method according to claim 1, wherein displaying in categories the multiple ultrasonic video data according to the respective category determined for each ultrasonic video data comprises:
displaying ultrasonic video data with a same category in a same display area; or
displaying ultrasonic video data with a same category in a same folder.

14. The method according to claim 1, further comprising:
arranging ultrasonic video data with a same category in order of examination time.

15. The method according to claim 1, wherein the category of each ultrasonic video data comprises a category of each ultrasonic video data determined by a first classification rule and a category of each ultrasonic video data determined by a second classification rule; and
displaying in categories the multiple ultrasonic video data according to the respective category determined for each ultrasonic video data comprises: selectively displaying in categories the multiple ultrasonic video data according to the category determined by the first classification rule or according to the category determined by the second classification rule in accordance with a received user instruction.

16. The method according to claim 15, wherein selectively displaying in categories the multiple ultrasonic video data according to the category determined by the first classification rule or according to the category determined by the second classification rule in accordance with the received user instruction comprises:
when displaying in categories the multiple ultrasonic video data according to the category determined by the first classification rule, switching to displaying in categories the multiple ultrasonic video data according to the category determined by the second classification rule when receiving a user instruction instructing to switch a mode of displaying in categories.

17. The method according to claim 9, wherein displaying in categories the multiple ultrasonic video data according to the respective category determined for each ultrasonic video data comprises:
displaying a body map on a display interface, different portions of the body map corresponding to different scanning parts, wherein the scanning part comprises a scanning organ, a scanning section, or a scanning area; and
displaying the multiple ultrasonic video data in association with corresponding portions of the body map according to the scanning parts of the representative frames of the multiple ultrasonic video data.

18. The method according to claim 17, wherein displaying the multiple ultrasonic video data in association with the corresponding portions of the body map according to the scanning parts of the representative frames of the multiple ultrasonic video data comprises:

displaying identifiers of the multiple ultrasonic video data at different portions of the body map.

19. A method for displaying ultrasonic data, comprising:

acquiring multiple ultrasonic data to be displayed, the multiple ultrasonic data including ultrasonic data of different tissue parts;

determining a respective category of each of the multiple ultrasonic data at least according to a scanning part of each of the multiple ultrasonic data, wherein the scanning part comprises a scanning organ, a scanning section, or a scanning area;

displaying a body map on a display interface, different portions of the body map corresponding to different scanning parts of the multiple ultrasonic data; and displaying the multiple ultrasonic data in association with corresponding portions of the body map according to the respective category determined for each of the multiple ultrasonic data.

20. A method for displaying ultrasonic data, comprising:

acquiring multiple ultrasonic data to be displayed, the multiple ultrasonic data including ultrasonic data of different tissue parts;

determining a respective category of each of the multiple ultrasonic data; and displaying in categories the multiple ultrasonic data according to the respective category determined for each of the multiple ultrasonic data, wherein displaying in categories the multiple ultrasonic data comprises displaying ultrasonic data with a same category in a same display area.

21. The method according to claim 20, wherein the ultrasonic data with the same category is arranged in order of examination time; or the respective category of each of the multiple ultrasonic data is determined according to at least one of: a scanning part corresponding to each of the multiple ultrasonic data, an imaging mode, a type of a user annotation item, a type of a user measurement item, and a type of an ultrasonic probe used to acquire the multiple ultrasonic data.

* * * * *